(12) United States Patent
Weber et al.

(10) Patent No.: US 6,533,818 B1
(45) Date of Patent: Mar. 18, 2003

(54) ARTIFICIAL SPINAL DISC

(75) Inventors: Paul J. Weber, Ft. Lauderdale, FL (US); Luiz B. Da Silva, Danville, CA (US)

(73) Assignee: Pearl Technology Holdings, LLC, Tampa, FL (US)

( * ) Notice: Subject to any disclaimer, the term of this patent is extended or adjusted under 35 U.S.C. 154(b) by 0 days.

(21) Appl. No.: 09/625,440

(22) Filed: Jul. 26, 2000

Related U.S. Application Data

(63) Continuation-in-part of application No. 09/558,896, filed on Apr. 26, 2000.

(51) Int. Cl.[7] .................................................. A61F 2/44
(52) U.S. Cl. ................................................... 623/17.16
(58) Field of Search ........................... 623/17.11, 17.12, 623/17.13, 17.16, 23.41, 23.5, 23.51, 23.52

(56) References Cited

U.S. PATENT DOCUMENTS

| | | | | | |
|---|---|---|---|---|---|
| 5,674,294 A | * | 10/1997 | Bainville et al. | ......... | 623/17.16 |
| 5,702,449 A | * | 12/1997 | McKay | ............ | 623/17.16 |
| 5,755,798 A | * | 5/1998 | Papavero et al. | ............ | 606/61 |
| 5,762,073 A | * | 6/1998 | Choy | ............ | 128/846 |
| 6,347,240 B1 | * | 2/2002 | Foley et al. | ............ | 600/426 |

* cited by examiner

*Primary Examiner*—David J. Isabella
*Assistant Examiner*—Hieu Phan
(74) *Attorney, Agent, or Firm*—John P. Wooldridge

(57) ABSTRACT

A multi layered artificial spinal disc that can be surgically implanted to replace a damaged natural spinal disc. The top and bottom layers being comprised of bone permeable material that when implanted would fuse to the vertebrae and form a permanent bond. The middle layer is a polymer with mechanical properties similar to natural spinal discs.

36 Claims, 2 Drawing Sheets

ARTIFICIAL SPINAL DISC

The present invention is a continuation-in-part of U.S. patent application Ser. No. 09/558,896 titled "Prosthetic Spinal Disc" filed Apr. 26, 2000, and incorporated herein by reference.

BACKGROUND OF THE INVENTION

1. Field of the Invention

The present invention relates to prosthetic devices, and more specifically, it relates to an artificial spinal disc for replacement of a natural spinal disc.

2. Description of Related Art

The vertebral spine is a complex arrangement of many structures, with many areas of specially cushioned apposition. The vertebral bones are twenty-four in number, not including the sacrum, and they gradually vary in size, shape and load distribution from the cervical to the thoracic to the lower lumbar vertebrae. The vertebrae, amazingly, are very different between the first cervical and the last lumbar vertebra. Nonetheless, the bony vertebral bodies of the spine are each separated by a relatively soft intervertebral disc that acts as a joint, allowing flexion, extension, lateral bending and axial rotation. Fibrous tissues, emulating scar tissues, may act somewhat similarly to the bonding elements that make up the ligaments of the spine, as well as the outer portions of the relatively soft intervertebral discs. If a synthetic vertebral disc were to be placed to repair one that is damaged, it would be beneficial to have the participation of these fibrous fixing elements in a relatively controlled and maximized fashion.

The typical vertebra has a thick interiorly located bone mass called the vertebral body (with a neural vertebral arch that arises from a posterior surface of the vertebral body). The intervertebral disc primarily serves as a mechanical cushion between the vertebral bones, permitting controlled motion within the vertebral segments of the.axial skeleton. The normal disc is a unique mixed structure, comprised of three component tissues, including the nucleus pulposus (nucleus), the annulus fibrosus (annulus), and the two opposing vertebral end plates. The two vertebral end plates are each composed of thin cartilage overlying a thin layer of hard cortical bone, which attaches to a spongy, richly vascular cancellous bone of the vertebral body. The vertebral end plates thus serve to attach the adjacent vertebra to the disc. In other words, a transition zone is created by the end plates between the malleable disc and the bony vertebra.

The annulus of the disc is a tough outer fibrous ring that binds together the adjacent vertebrae. The fibrous portion is much like a laminated automobile tire measuring about 10 to 15 mm in height and about 15 to 20 mm in thickness. Fibers of the annulus consist of 15 to 20 overlapping multiple plies and are attached at the superior and inferior vertebral body at a roughly 30-degree angle in both directions. This configuration particularly resists torsion, as about half of the angulated fibers will tighten when the vertebrae rotate in either direction relative to each other.

Inside the annulus there is a relatively liquid core, the nucleus. The healthy natural nucleus has a high water content and aids in the load bearing and cushioning properties of the spinal disc; however, the spinal disc may be displaced or damaged due to trauma or disease. A disc herniation occurs when the annulus fibers are weakened or torn and the nucleus becomes permanently stressed, extended or extruded out of its normal internal annular confines. A herniated or slipped nucleus can compress a spinal nerve posteriorly, resulting in pain, loss of muscle control or even paralysis. Alternatively, in disc degeneration the nucleus loses its water binding capacity and deflates as though the air had been let out of a tire. Subsequently, height of the nucleus decreases, causing the annulus to buckle in areas where the laminated plies are loosely bonded. As the overlapping laminated plies of the annulus begin to buckle and separate, either circumferential or radial annular tares may occur and contribute to persistent and disabling pain. Adjacent ancillary spinal facet joints to the rear may also be forced into an overriding position, which may cause additional back pain as tissues are damaged due to irregular contact and force application.

Upon identification of the abnormality causing the conduction disorders, surgery may be required to correct the problem if more conservative treatment fails. For those problems associated with the formation of osteophytes or herniations of the intervertebral disc, one such surgical procedure is intervertebral discectomy. In this procedure, the involved vertebral bodies are exposed and the invertebral disc is removed, thus removing the offending tissue or providing access for the removal of the bone osteophytes. A second procedure, termed a spinal fusion, may then be required to fix the vertebral bodies together to prevent movement and maintain the space originally occupied by the intervertebral disc. Some minor loss of flexibility in the spine may result, but because of the large number of vertebrae the loss of mobility is usually acceptable.

During spinal fusion following a discectomy, an implant is inserted into the intervertebral space. This intervertebral implant is often a bone graft removed from another portion of the patient's body, termed an autograft. The use of bone taken from the patient's body has the important advantage of avoiding rejection of the implant, but has some shortcomings. There is always a risk in opening a second surgical site for obtaining the bone graft, which can lead to infection or pain for the patient, and the site of the bone graft is weakened by the removal of bony material. The bone implant may not be perfectly shaped and placed, leading to slippage or absorption of the implant, or failure of the implant to fuse with the vertebrae.

Other options for a graft source for the implant are bone removed from cadavers, termed an allograft, or from another species, termed a xenograft. In these cases, while there is the benefit of not having a second surgical site as a possible source of infection or pain, there is the increased difficulty with graft rejection and the risk of transmitting communicable diseases.

An alternative approach to using a bone graft is to use a manufactured implant made of a synthetic material that is biologically compatible with the body and the vertebrae. Several compositions and geometries of such implants have been utilized, ranging from simple blocks of material to carefully shaped implants, with varying success. No fully satisfactory implant has been reported. In some instances, the implanting surgery is readily accomplished, but the results are unsatisfactory due to side effects or dislocation of the implant In other instances, the implant requires a complex surgical procedure that is difficult to perform and still may not lead to correction of the problem for the reasons indicated.

In U.S. Pat. Nos. 5,306,309 and 5,683,464 by Wagner et al., the authors provide a solid body spinal disc implant and surgical implantation kit. This solid body implant is made of a biocompatible synthetic material designed to engage the cortical bone region of the vertebrae after implantation. This type of implant does not address the central portion of the vertebral body region made of cancellous bone. It would be advantageous to have an implant with a central layer similar to this more resilient and less dense type of bone. A multi-layered design that mimics the mechanical properties of a natural spinal disc is desirable.

U.S. Pat. No. 5,123,926 by Pisharodi discusses a disc prosthesis composed of biologically compatible material. This prosthesis could be implanted and expanded to conform to the vertebral space so as to replicate a natural disc's function. Expansion would be achieved by injecting a liquid or gas substance through a port into the disc prosthesis. While this would provide a tight fit in the disc space, problems could arise should the prosthesis rupture.

There is a need for a truly stable yet fully flexible artificial spinal disc, which could be utilized, in a surgical procedure with a high probability of success without producing undesirable side effects. The present invention fulfills this need, and further provided related advantages.

SUMMARY OF THE INVENTION

It is an object of the present invention to provide a multi layered artificial spinal disc that can be used to replace a damaged natural spinal disc. This and other objects of the invention will be apparent from the teachings of the present invention.

The artificial spinal disc of the present invention is comprised of biocompatible materials that when implanted will respond similarly to a natural disc. Using a computed tomography (CT) scan, ultrasound imaging, and/or magnetic resonance imaging (MRI) the artificial disc can be shaped to meet a patient's specific needs. Through imaging, the artificial disc can be contoured to fit the bony irregularities present in the spine to produce a tight fit and provide for maximum bone to implant bonding.

The implant is designed to approximate the size and shape of a natural vertebral disc. This implant is comprised of three distinct layers. The top and bottom layers are made of bone permeable material such as porous titanium. Use of bone permeable materials promotes permanent bonding between the artificial disc and the spine bone. The central layer of the implant is comprised of biocompatible polymers that mimic the mechanical properties of natural discs. To further duplicate the mechanical properties of natural discs the middle portion of the central layer can be composed of softer material (e.g., silicon rubbers and/or polyurethane/silicon composites) and surrounded by the central layer of biocompatible polymer.

The present invention provides a strong bond between the different layers of the implant. This can be achieved by pressure injection of the polymer into the porous titanium. The top and bottom layers of the implant can also be machined with precision cutting machines or lasers to produce trapping structures thinly coated with porous titanium to promote bone in-growth between the implant and the spine.

The thickness of the hard top and bottom layer of the implant can be uniform or vary in thickness to modify compressibility of the disc. During the surgical procedure, it may be necessary to mechanically scrape the vertebral bone to produce a clean planar surface and cause a strong vertebral bone-to-implant bond to form. To increase bonding, bone growth factors can be applied to the implant or vertebral bone during surgery. Following surgery, motion may need to be limited to allow time for proper bonding to occur.

The invention provides an artificial spinal disc with a lip contoured into the hard top and bottom layer. The lip on the implant can be packed with a paste form of artificial bone that fills in gaps between the implant and the vertebral bone. The lip also limits lateral motion and accurately locates the disc.

An alternative embodiment of the present invention has an annular region on the top and bottom bone permeable surface designed to bond to the hard cortical bone of the vertebra. To produce the desired mechanical properties, the core of the implant is comprised of compressible biocompatible polymer. The compressible core is held in place by a high strength, less compressible outer support made of polymers or composites. This outer support prevents excessive movement of the outer surface that could put pressure on the spinal cord or nerves. Carbon fibers can be embedded in the composite material and by varying the orientation of the fibers; it is possible to duplicate the properties of the natural disc annulus fibrosus.

Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description serve to explain the principles of the invention.

DETAILED DESCRIPTION OF THE INVENTION

Figure 1:
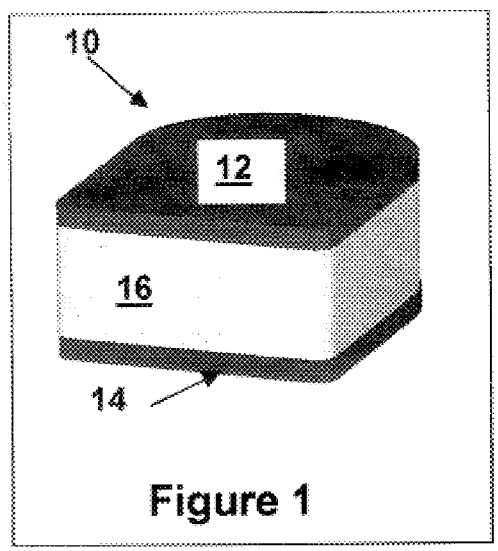
FIG. 1 shows one embodiment of the present invention comprised of three distinct layers.

FIG. 1 shows a perspective view of one embodiment of the artificial spinal disc implant The implant 10 is designed to approximate the shape and size of natural intervertebral discs. It has a planar top 12 and bottom 14 that bond to the vertebral bone when implanted in the vertebral spine. The implant is comprised of three distinct layers including a central layer 16.

Figure 2:
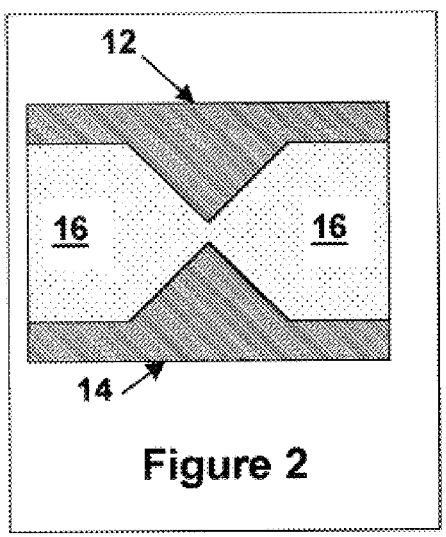
FIG. 2 shows a cross sectional view through the center of an embodiment of the implant using bone permeable material for the top and bottom layers. The central layer is composed of biocompatible material.
Figure 3:
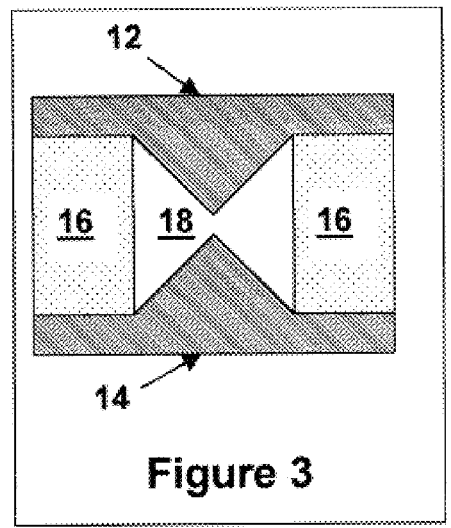
FIG. 3 is an alternative embodiment of the present invention with the central layer composed of multiple materials.

FIG. 2 shows a cross sectional view through the center of the implant The implant has a top layer 12 and bottom layer 14 that are made of bone permeable material. When implanted in the spine, bone will grow into these layers to form a strong bond that prevents the disc from moving. One such bone permeable material to use for the top 12 and bottom 14 layers is porous titanium. Porous titanium is currently used in artificial hip and knee joints to provide a permanent bond between the metallic implants and the surrounding bone. Alternative materials that can be used for the top 12 and bottom 14 layers include ceramics and glass ceramics. Hydroxyapatite and polycrystalline alumina ($Al_2O_3$) coated metals can also be used for the top 12 and bottom 14 layers. The central layer 16 of the implant is composed of biocompatible material that has similar mechanical properties to natural discs. Examples of biocompatible polymers that can be used for this layer include polyurethane, polydimethyl siloxane, polyvinyl chloride (PVC), polyethylene and teflon. The central layer 16 can be composed of a single material as shown in FIG. 2 or multiple materials as shown in FIG. 3. In FIG. 3, the middle section 18 of the central layer is composed of a softer material that matches the mechanical properties of the nucleus in natural discs. Possible materials for this section include silicon rubbers, hydrogels and polyurethane/silicon composites.

Figure 4:
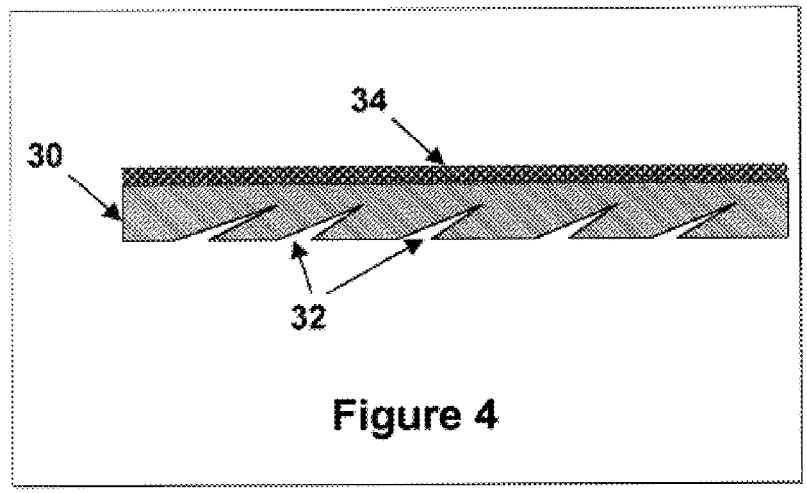
FIG. 4 shows an alternative embodiment of the present invention with machined top and bottom layers to aid bone growth.

It is critical that strong bonding exists between the three different layers-in the implant. By pressure injection of the polymer into the porous titanium, bonding over a large surface area will be possible. In addition, the top 12 and bottom 14 layers could be manufactured as shown in FIG. 4. This bone permeable layer is composed of a solid titanium segment 30 with polymer trapping structures 32 over coated with a thin porous titanium layer 34 for bone in-growth. These miniature structures can be machined using precision cutting machines or lasers.

Figure 5:
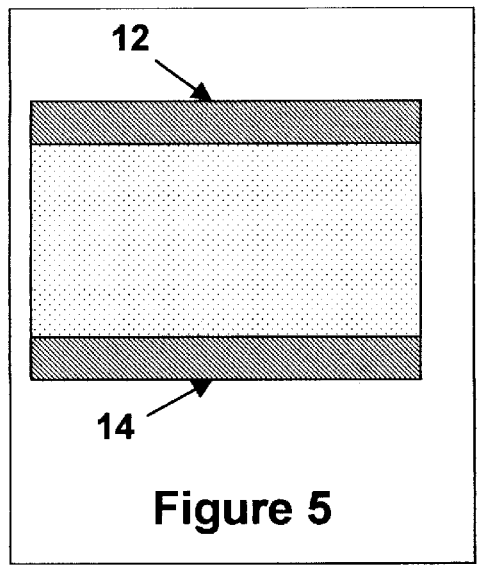
FIG. 5 shows an example of the present invention with uniform top and bottom layers.
Figure 6:
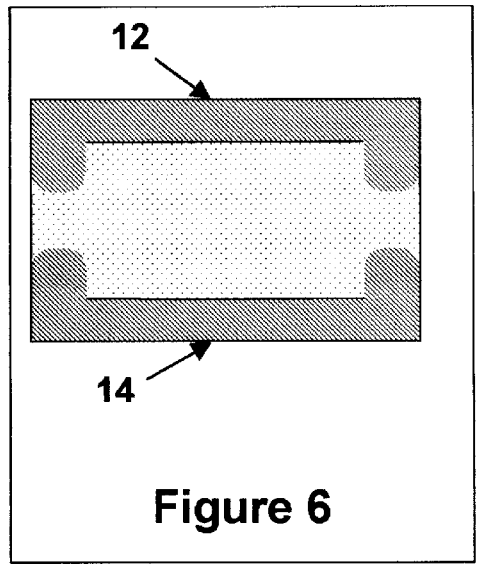
FIG. 6 shows an alternative to the present invention as illustrated in FIG. 2 with top and bottom layers that can vary in thickness.

The thickness of the hard top 12 and bottom 14 layers can be uniform across the implant surface as shown in FIG. 5, or the thickness can vary as shown in FIG. 2 and FIG. 6 to modify the compressibility of the disc.

During normal use of this implant, it may be necessary to prevent motion to allow sufficient time for significant bone growth into the top 12 and bottom 14 layers. Excessive motion would likely prevent a strong vertebral bone-to-implant bond to form. Bone growth factors can be applied to the implant or vertebral bone during the surgical procedure to accelerate the bonding. In addition, to ensure that the implant mates properly with the vertebral bone, it may be necessary to mechanically scrape the vertebral bone to produce a clean planar surface.

Figure 7:
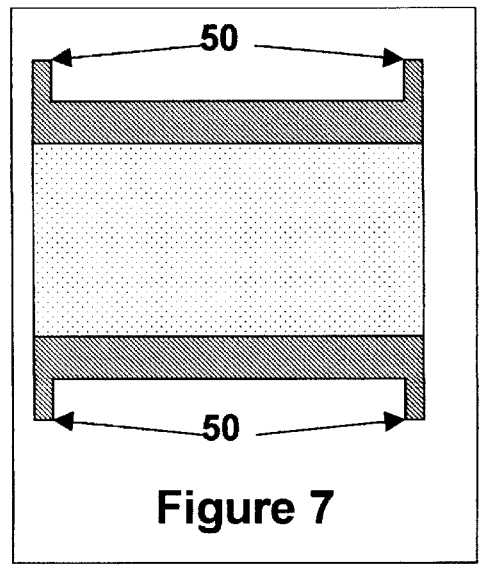
FIG. 7 is an alternative embodiment of the invention with a lip that can be packed with artificial bone to fill gaps between the implant and vertebral bone.

In another embodiment of the implant as shown in FIG. 7, a lip 50 on the device forms a compartment that can be packed with hydroxyapatite paste or powdered bone mixtures that will act to fill in gaps between the implant and vertebral bone.

Figure 8:
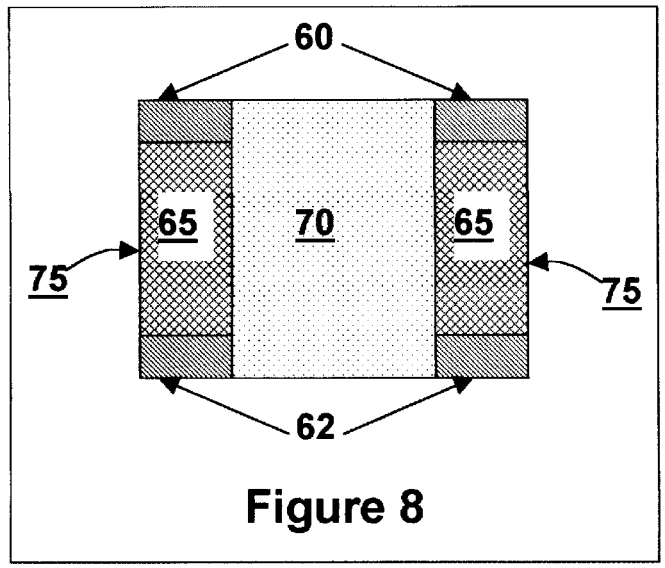
FIG. 8 shows a cross sectional view of an alternative embodiment of the present invention with an annular region on the top and bottom and biocompatible polymer core.

FIG. 8 shows a cross sectional view of an alternative embodiment that has an annular region on the top 60 and bottom surface 62 of bone permeable material. The annular region is designed to bond to the hard cortical bone of the vertebra. A compressible biocompatible polymer (e.g., polydimethyl siloxane, polyethylene, polyurethane) forms the core 70 of the artificial disc. The core 70 could also be made of biocompatible hydro gel (e.g., polyhydroxyethyl methacrylate PHEMA). The mechanical properties of hydro gels can be varied to achieve the desired mechanical properties. The compressible core 70 is constrained by a high tensile strength and less compressible outer support 65. This outer support 65 limits the compressibility and prevents the outer surface 75 from excessive bulging that could put pressure on the spinal cord or nerves. The outer support 65 can be made of high strength polymers such as polyurethane or composites. Possible composites include ultra high molecular weight polyethylene with embedded carbon fibers. By varying the orientation of the fibers it is possible to simulate the properties of the natural disc annulus fibrosus.

In the present invention, the use of computed tomography (CT), ultrasound imaging and/or magnetic resonance imaging (MRI) enables the use of the bony irregularities of the vertebrae to create a tight fit for the spinal disc. When soft doughnut-like discs degenerate in between the bony vertebrae above and below, there are usually other problems with the plates and, therefore, the shapes of the vertebrae above and below are abnormally shaped. The plates usually become spurred, burred, and curved and are not very flat unless the surgeon sands them down. Thus, the present invention provides stereo tactic forming, either manually or automated, using a CAT scanner, MRI or three-dimensional ultrasound in order to shape a prosthetic spinal disc. This will simulate the outer portion of the natural disc (annulus).

The imaging of the vertebrae is used to determine the abutting vertebrae dimensions and their conformations to which the implant may be contoured either by a computer-controlled robotic mechanism or by manual reduction.

Additionally, contouring may be planned in the area of the abutting vertebral bony bodies, which may be used in combination with the manual or automated contouring that will take place upon the prosthesis prior to surgery. Then the prosthetic manipulation would likely be in a laboratory prior to surgery, and the human body vertebral bony area manipulation would take place at the time of surgery. Either could be computer or manually controlled. Nonetheless, the three-dimensional contouring needs would be assessed and pre-planned by the use of MRI, three-dimensional ultrasound imaging and/or CT imaging.

WO 89/11257, titled "Method And System For Making Prosthetic Device", incorporated herein by reference, is directed to a method of making a prosthetic device or a three-dimensional object having surface characteristics derived from data obtained from a patient and from data created to modify the surface characteristics of the object. Such data is obtained by sensing the object by transducer. A solid modeling system with memory and a processor, and process control elements construct three dimension data files based upon mathematical creation of the solid model with cuberille data. Various transducers are illustrated, including free wand transducers of plane image location and xyz coordinate location of subject elements, and a system for sampling data from ultrasound, a CT scan, a Magnetic Resonant Imaging (MRI) scan and other techniques, along with surgical methods of treatment and diagnosis. The information in WO 89/11257 is one example of a method of forming a three dimensional object based on imaging with CT, ultrasound and/or magnetic resonance. Other methods of three-dimensional fabrication based on these imaging techniques are known in the art and are within the scope of the present invention.

The foregoing description of the invention has been presented for purposes of illustration and description and is not intended to be exhaustive or to limit the invention to the precise form disclosed. Many modifications and variations are possible in light of the above teaching. For example, although the present invention provides for a prosthetic human intervertebral disc, this disc may be used for racehorses and other animals of value. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

We claim:

1. An artificial spinal disc, comprising:
   a first annular layer of biocompatible bone permeable material, wherein said first annular layer comprises a first central opening;
   a second annular layer of biocompatible bone permeable material, wherein said second annular layer comprises a second central opening;
   a core having a first end affixed within said first central opening and having a second end affixed within said second central opening, wherein said core comprises biocompatible material; and
   an outer support surrounding and constraining said core, wherein said outer support comprises a tensile strength that is greater than the tensile strength of said core, wherein said outer support limits the compressibility and prevents the outer surface of said outer support from excessive bulging that could put pressure on the spinal cord or nerves,
   wherein at least one of said first annular layer and said second annular layer comprises an annular region of bone permeable material, wherein said annular region is designed to bond to the hard cortical bone of a vertebra, wherein said core comprises a material selected from the group consisting of a compressible biocompatible polymer and a biocompatible hydrogel,
   wherein said outer support comprises high strength polymers selected from the group consisting of polyurethane and composite material, and
   wherein said composite material comprises ultra high molecular weight polyethylene with embedded carbon fibers.

2. The artificial spinal disc of claim 1, wherein at least one of said first annular layer and said second annular layer is planar.

3. The artificial spinal disc of claim 1, wherein at least one of said first annular layer and said second annular layer comprises biocompatible bone permeable material selected from the group consisting of porous titanium, ceramic, glass ceramic, hydroxyapatite and metal coated with polycrystalline alumina ($Al_2O_3$).

4. The artificial spinal disc of claim 1, wherein said core comprises biocompatible polymer.

5. The artificial spinal disc of claim 4, wherein said biocompatible polymer is selected from the group consisting of polyurethane, polydimethyl siloxane, polyvinyl chloride (PVC), polyethylene and teflon.

6. The artificial spinal disc of claim 1, wherein said core comprises a plurality of materials.

7. The artificial spinal disc of claim 1, wherein said core comprises a central disc of material that diverges from the center of said artificial spinal disc.

8. The artificial spinal disc of claim 7, wherein said central disc of material comprises material selected from the group consisting of silicon rubber, polyurethane/silicon composite and hydrogel.

9. The artificial spinal disc of claim 1, wherein at least one of said first annular layer and said second annular layer comprises a uniform thickness.

10. The artificial spinal disc of claim 1, further comprising bone growth factors applied to at least one of said first annular layer and said second annular layer.

11. The artificial spinal disc of claim 1, wherein said core comprises compressible biocompatible polymer selected from the group consisting of polydimethyl siloxane, polyethylene, polyurethane, silicon rubber compounds and teflon.

12. The artificial spinal disc of claim 1, wherein said core comprises biocompatible hydrogel selected from the group consisting of polyhydroxyethyl methacrylate (PHEMA), polyacrylamides, polyvinyl alcohol, PNVP and hydrogel that uses methacrylic acid as monomers.

13. The artificial spinal disc of claim 1, wherein said core comprises biocompatible hydrogel having a compressibility that can be varied to achieve the desired mechanical properties.

14. The artificial spinal disc of claim 1, wherein the orientation of said embedded carbon fibers is varied to simulate the properties of the natural disc annulus fibrosus.

15. The artificial spinal disc of claim 1, wherein at least one of said first annular layer and said second annular layer is contoured to substantially correspond to a surface of a vertebrae against which at least one of said first annular layer and said second annular layer will be located.

16. The method of claim 1, further comprising surgically shaping the vertebrae above and/or below said first annular layer and said second annular layer to substantially correspond to at least one of said first annular layer and said second annular layer.

17. A method for making an artificial spinal disc, comprising:
   forming a first annular layer of biocompatible bone permeable material, wherein said first annular layer comprises a first central opening;
   forming a second annular layer of biocompatible bone permeable material, wherein said second annular layer comprises a second central opening;
   forming a core of biocompatible material;
   affixing a first end of said core within said first central opening;
   affixing a second end of said core within said second central opening; and
   forming an outer support surrounding and constraining said core, wherein said outer support comprises a tensile strength that is greater than the tensile strength of said core, wherein said outer support limits the compressibility and prevents the outer surface of said outer support from excessive bulging that could put pressure on the spinal cord or nerves,
   wherein at least one of said first annular layer and said second annular layer comprises is designed to bond to the hard cortical bone of a vertebra, wherein said core comprises a material selected from the group consisting of a compressible biocompatible polymer and a biocompatible hydrogel,
   wherein said outer support comprises high strength polymers selected from the group consisting of polyurethane and composite material, and
   wherein said composite material comprises ultra high molecular weight polyethylene with embedded carbon fibers.

18. The method of claim 17, wherein at least one of said first annular layer and said second annular layer is planar.

19. The method of claim 17, wherein at least one of said first annular layer and said second annular layer comprises biocompatible bone permeable material selected from the group consisting of porous titanium, ceramic, glass ceramic, hydroxyapatite and metal coated with polycrystalline alumina ($Al_2O_3$).

20. The method of claim 17, wherein said core comprises biocompatible polymer.

21. The method of claim 20, wherein said biocompatible polymer is selected from the group consisting of polyurethane, polydimethyl siloxane, polyvinyl chloride (PVC), polyethylene and teflon.

22. The method of claim 17, wherein said core comprises a plurality of materials.

23. The method of claim 17, wherein said core comprises a central disc of material that diverges from the center of said artificial spinal disc.

24. The method of claim 23, wherein said central disc of material comprises material selected from the group consisting of silicon rubber, polyurethane/silicon composite and hydrogel.

25. The method of claim 17, wherein at least one of said first annular layer and said second annular layer comprises a uniform thickness.

26. The method of claim 17, further comprising applying bone growth factors to said at least one of said first annular layer and said second annular layer comprises.

27. The method of claim 17, wherein at least one of said first annular layer and said second annular layer comprises is designed to bond to the hard cortical bone of a vertebra, wherein said core comprises a material selected from the group consisting of a compressible biocompatible polymer and a biocompatible hydrogel.

28. The method of claim 27, wherein said compressible biocompatible polymer is selected from the group consisting of polydimethyl siloxane, polyethylene, polyurethane, silicon rubber compound and teflon.

29. The method of claim 27, wherein said biocompatible hydrogel is selected from a group consisting of polyhydroxyethyl methacrylate (PHEMA) and polyacrylamides, polyvinyl alcohols, PNVP and hydrogels that use methacrylic acid as monomers.

30. The method of claim 27, wherein said biocompatible hydrogel comprises a compressibility that can be varied to achieve the desired mechanical properties.

31. The method of claim 27, further comprising forming an outer support surrounding and constraining said core, wherein said outer support comprises a tensile strength that is greater than the tensile strength of said core, wherein said outer support limits the compressibility and prevents the outer surface of said outer support from excessive bulging that could put pressure on the spinal cord or nerves.

32. The method of claim 31, wherein said outer support comprises high strength polymers selected from the group consisting of polyurethane and composite material.

33. The method of claim 32, wherein said composite material comprises ultra high molecular weight polyethylene with embedded carbon fibers.

34. The method of claim 17, wherein the orientation of said embedded carbon fibers is varied to simulate the properties of the natural disc annulus fibrosus.

35. The method of claim 17, wherein at least one of said first annular layer and said second annular layer is contoured to substantially correspond to a surface of a vertebrae against which said top and bottom layer will be located.

36. The method of claim 35, further comprising obtaining values for contouring at least one of said first annular layer and said second annular layer, wherein said values are obtained with a machine selected from the group consisting of a magnetic resonance imaging machine, a computed tomography machine and an ultrasound imaging machine.

* * * * *